United States Patent [19]

Heavner

[11] Patent Number: 5,641,751
[45] Date of Patent: Jun. 24, 1997

[54] TUMOR NECROSIS FACTOR INHIBITORS

[75] Inventor: George A. Heavner, Malvern, Pa.

[73] Assignee: Centocor, Inc., Malvern, Pa.

[21] Appl. No.: 432,694

[22] Filed: May 1, 1995

[51] Int. Cl.$^6$ .............................. A61K 38/00; C07K 7/00
[52] U.S. Cl. .................. 514/13; 514/12; 514/14; 514/15; 514/16; 514/17; 514/18; 530/324; 530/325; 530/326; 530/327; 530/328; 530/329; 530/330
[58] Field of Search ................. 514/12–18; 530/327, 530/328, 329, 330, 326

[56] References Cited

U.S. PATENT DOCUMENTS

| 4,920,196 | 4/1990 | Aggarwal | 530/351 |
| 5,519,000 | 5/1996 | Heavner et al. | 514/12 |

FOREIGN PATENT DOCUMENTS

| 398327 | 11/1990 | European Pat. Off. . |
| 2258324 | 11/1987 | Japan . |
| 194594 | 8/1993 | Japan . |
| 9002566 | 3/1990 | WIPO . |
| 9107418 | 5/1991 | WIPO . |
| 9211018 | 7/1992 | WIPO . |
| 9211383 | 7/1992 | WIPO . |
| 9215683 | 9/1992 | WIPO . |
| WO93/06128 | 4/1993 | WIPO . |

OTHER PUBLICATIONS

Dayhoff, Atlas of Protein Sequence and Structure, vol. 5, 1972, Fig. 9–12, p. 96.
Kaartinen et al., Nature, 304: 320–324 (1983).
Stark et al., J. Exp. Med., 174: 613–624 (1991).
Aderka, et al., "Stabilization of the Bioactivity of Tumor Necrosis Factor by its Soluble Receptors", J. Exp. Med. 1992, 175, 323–329.
Alvaro–Gracia et al., "Cytokines in Chronic Inflammatory Arthrities", J. of Immunol. 1991, 146, 3365–3371.
ASM News 1990, 56, 368.
Bennett, "The Etiology of Rheumatoid Arthritis", in Textbook for Rheumatology, Kelley et al., eds., W.B. Saunders, Philadelphia, Chap. 58, pp. 879–886, 1985.
Beutler et al., "The Biology of Cachectin/TNF—A Primary Mediator of the Host Response", Ann. Rev. Immunol. 1989, 7, 625–655.
Bodanszky et al, "Peptide Synthesis", John Wiley & Sons, 2nd Ed., 1976.
Brennan et al., "Inhibitory Effect of TNF alpha Antibodies on Synovial Cell Interleukin–1 Production in Rheumatoid Arthritis", Lancet 1989, 244–247.
Buchan et al., "Interluekiln–1 and Tumour Necrosis Factor mRNA Expression in Rheumatoid Arthritis; Prolonged Production of IL–1 Alpha", Clin. Exp. Immunol. 1988, 73, 440–455.
Butera et al., "Regulation of HIV–1 Expression by Cytokine Networks in a CD4$^+$ Model of Chronic Infection", J. Immunology 1993, 150, 625–634.

Camussi et al., "Tumor Necrosis Factor/cachectin Stimulates Peritoneal Macrophages, Polymorphonuclear Neutrophils, and Vascular Endothelial Cells to Synthesize and Release Platelet–activating Factor", J. Exp. Med. 1987, 166, 1390–1404.
Carswell et al., "An Endotoxin–induced Serum Factor that Causes Necrosis of Tumors", PNAS USA 1975, 72, 3666–3670.
Cerami et al., "The Role of Cachectun/TNF in Endotoxic Shock and Cachexia", Immunol. Today 1988, 9, 28–31.
Debets et al., "The Role of Tumor Necrosis Factor/Cachectin in Septic Shock", Second Vienna Shock Forum 1989, 463–466.
Elliott, M. et al., "Randomised Double–blind Comparison of Chimeric Monoclonal Antibody to Tumour Necrosis Factor α (cA2) Versus Placebo in Rheumatoid Arthritis", The Lancet 1994, 344, 1105–1110.
Elliott, M. et al., "Repeated Therapy with Monoclonal Antibody to Tumour Necrosis Factor α (cA2) in Patients with Rheumatoid Arthritis", The Lancet 1994, 344, 1125–1127.
Espevik et al., "A Highly Sensitive Cell Line, WEHI 164 Clone 13, for Measuring Cytotoxic Factor/Tumor Necrosis Factor From Human Monocytes",. J. Immunol. Methods 1986.
Fiers, "Characterization at the Molecular Cellular and in vivo Level", FEBS Letters 1991, 285, 199–212.
Goeddel et al., "Tumor Necrosis Factors: Gene Structure and Biological Activities", Spring Harbor Symp. Quant. Biol. 1986, LI, 597–609.
Gray, P. et al., "Cloning of Human Tumor Necrosis Factor (TNF) Receptor cDNA and Expression of Recombinant Soluble TNF–binding Protein", PNAS USA 1990, 87, 7380.
Harris, "Rheumatoid Arthritis: The Clinical Spectrum", in Textbook of Rheumatology, Kelley et al., eds., W.B. Saunders, Philadelphia, Ch. 60, pp. 915–990, 1985.
Haworth et al., "Expression of Granulocyte–macrophage Colony–stimulating Factor in Rheumatoid Arthritis: Regulation by Tumor Necrosis Factor–alpha", Eur. J. Immunol. 1991, 21, 2575–2579.
Hofmann, S. et al., "Molecular Cloning of a Histidine–rich $Ca^{2+}$–binding Protein of Sarcoplasmic Reticulum That Contains Highly Conserved Repeated Elements", J. of Biol. Chem. 1989, 264, 18083–18090.
Jaroff, L., "Stop That Germ!" Time 1988, May 23, 56.
Kent, S. et al., "Modern Methods for the Chemical Synthesis of Biologically Active Peptides", in Synthetic Peptides in Biology and Medicine, Alitalo et al., eds., Science Publishers, Amsterdam, pp. 29–57, 1985.

(List continued on next page.)

Primary Examiner—Cecilia J. Tsang
Assistant Examiner—C. Delacroix-Muirheid
Attorney, Agent, or Firm—Woodcock Washburn Kurtz Mackiewicz & Norris LLP

[57] ABSTRACT

Peptides which consist of 4–25 amino acids and which bind to tumor necrosis factor-alpha, prevent tumor necrosis factor-alpha from binding to its receptors and inhibit tumor necrosis factor-alpha activity are disclosed. Methods of inhibiting tumor necrosis factor-alpha activity and of treating individuals suffering from tumor necrosis factor-alpha-mediated diseases and disorders are disclosed.

9 Claims, No Drawings

OTHER PUBLICATIONS

Kern et al., "Cancer Cachexia", *J. Parent. Enter. Nutr.*, 1988, 12, 286–298.

Kohno, T. et al., "A Second Tumor Necrosis Factor Receptor Gene Product can Shed a Naturally Occurring Tumor Necrosis Factor Inhibitor", *PNAS USA* 1990, 87, 8331.

Kornbluth et al., "Tumor Necrosis Factor Produciton by Human Monocytes is a Regulated Event: Induction of TNF–alpha–mediated Cellular Cytoxicity by Endotoxin", *J. Immunol.* 1986, 137, 2585–2591.

Kriegler et al., "A Novel Form of TNF/Cachectin is a Cell Surface Cytotoxic Transmembrane Protein: Ramifications for the Complex Physiology of TNF", *Cell* 1988, 53, 45–53.

Merrifield, "Solid Phase Peptide Synthesis. I. the Synthesis of a Tetrapeptide", *J. Am. Soc.* 1963, 15, 2149–2154.

Michie et al., "Tumour Necrosis Factor and Bacterial Sepsis", *Br. J. Surg.* 1989, 76, 670–671.

Michie et al., "Tumor Necrosis Factor and Endotoxin Induce Similar Metabolic Responses in Human Beings", *Surgery* 1988, 104, 280–286.

Michie et al., "Chronic TNF Infusion Causes Anorexia but Not Accelerated Nitrogen Loss", *Ann. Surg.* 1989, 209, 19–24.

Michie et al., "Detection of Circulating Tumor Necrosis Factor After Endotoxin Administration", *N. Eng. J. Med.* 1988, 318, 1481–1486.

Natanson, C. et al., "Selected Treatment Strategies for Septic Shock Based on Proposed Mechanisms of Pathogenesis", *Ann. Intern. Med.* 1994, 120, 771–783.

Oliff, "The Role of Tumor Necrosis Factor (Cachectin) in Cachexia", *Cell* 1988, 54, 141–142.

Oliff et al., "Tumors Secreting Human TNF/Cachectin Induce Cachexia in Mice", *Cell* 1987, 50, 555–563.

Piguet et al., "Tumor Necrosis Factor/Cachectin is an Effector of Skin and Gut Lesions of the Acute Phase of Graft–vs.–host Disease", *J. Exp. Med.* 1987, 166, 1280–1289.

Pober et al., "Two Distinct Monokines, Interleukin 1 and Tumor Necrosis Factor, Each Independently Induce Biosynthesis and Transient Expression of the Same Antigen on the Surface of Cultured Human Vascular Endothelial Cells", *J. Immunol.* 1986, 136, 1680–1687.

Pober et al., "Activation of Cultured Human Endothelial Cells by Recombinant Lymphotoxin: Comparison with Tumor Necrosis Factor and Interleukin 1 Species", *J. Immunol.* 1987, 138, 3319–3324.

Poli et al., "Tumor Necrosis Factor Alpha Function in an Autocrine Manner in the Induction of Human Immunodeficiency Virus Expression", *PNAS USA* 1990, 87, 782–785.

Porteu et al., "Shedding of Tumor Necrosis Factor Receptors by Activated Human Neutrophils", *J. Exp. Med.* 1990, 172, 599–607.

Pujol–Borrell et al., "HLA Class II Induction in Human Islet Cells by Interferon–y Plus Tumour Necrosis Factor of Lymphotoxin", *Nature* 1987, 326, 304–306.

Revhaug et al., "Inhibition of Cyclo–oxygenase Attenuates the Metabolic Response to Endotoxin in Humans", *Arch. Surg.* 1988, 123, 162–170.

Sandstrom, E. et al., "Antiviral Therapy in AIDS: Clinical Pharmacological Properties and Therapeutic Experience to Date", *Drugs* 1987, 34, 372–390.

Silva et al., "Prophylactic and Therapeutic Effects of a Monoclonal Antibody to Tumor Necrosis Factor–alpha in Experimental Gram–Negative Shock", *J. Inf. Sis.* 1990, 162, 421–427.

Simpson et al., "Role of Tumor Necrosis Factor in Sepsis and Acute Lung Injury", *Crit. Care Clin.* 1989, 5, 27–47.

Smith et al., "The Active Form of Tumor Necrosis Factor is a Trimer", *J. Biol. Chem.* 1987, 262, 6951–6954.

Tracey et al., "Anti–cachectin/TNF Monoclonal Antibodies Prevent Septic Shock During Lethal Bacteramia", *Nature* 1987, 330, 662–664.

Waage et al., "Association Between Tumour Necrosis Factor in Seruma dn Fatal Outcome in Patients with Meningococcal Disease", *The Lancet* 1987, 1, 355–357.

Wide, "Solid Phase Antigen–Antibody Systems", in Radioimmune Assay Method, Kirkham, ed., E & S Livingstone, Edinburgh, 1970, pp. 405–412

Williams et al., "Anti–tumor Necrosis factor Ameliorates Joint Disease in Murine Collagen–induced Arthritis", *PNAS USA* 1992, 89, 9784–9788.

Eilat, D. et al., "V Region Sequences of Anti–DNA and Anti–RNA Autoantibodies from NZB/NZW $F_1$ Mice", *J. Immunol.* 1988, 141, 1745–1753.

Foon, K.A., "Biological Response Modifiers: The New Immunotherapy", *Cancer Res.* 1989, 49, 1621–1639.

TUMOR NECROSIS FACTOR INHIBITORS

FIELD OF THE INVENTION

The present invention relates to compounds that inhibit tumor necrosis factor-alpha (TNFα) activity by binding to TNF-α and thereby preventing the TNFα from binding to TNF receptors. Thus, TNFα activity which is mediated through its binding to its receptor on cells is inhibited.

BACKGROUND OF THE INVENTION

The cytokine known as tumor necrosis factorα (TNFα; also termed cachectin) is a protein secreted primarily by monocytes and macrophages as a soluble homotrimer of 17 kD protein subunits in response to endotoxin or other stimuli (Smith, R. A. et al., J. Biol. Chem. 1987, 262, 6951–6954). A membrane-bound 26 kD precursor form of TNFα has also been described (Kriegler, M. et al., Cell 1988, 53, 45–53). TNFα was originally discovered in the serum of animals injected sequentially with a bacterial vaccine (bacillus Calmette-Guerin, BCG) and endotoxin (Carswell, E. A. et al., Proc. Natl. Acad. Sci. U.S.A 1975, 72, 3666).

The expression of the gene encoding TNFα is not limited to cells of the monocyte/macrophage family. Several human non-monocytic tumor cell lines were shown to produce TNFα. TNFα is also produced by $CD4^+$ and $CD8^+$ peripheral blood T lymphocytes, and by various cultured T and B cell lines.

TNFα plays an integral role in destroying tumors, mediating responses to tissue injury, and protecting hosts from infections by various microorganisms (Goeddel et al., Cold Spring Harbor Symp. Quant. Biol. 1986, 51, 597–609; Beutler et al., Ann. Rev. Immunol. 1989, 7, 625–655; Malik et al. in Tumor Necrosis Factor: Structure, Function and Mechanism of Action, Aggarwal and Vilcek, Eds. (Marcel Dekker, Inc., 1992); Fiers, FEBS Letters 1991, 285, 199–212; and Buetler etal., Buetler, B., Ed. in Tumor Necrosis Factors: the Molecules and Their Emerging Role in Medicine (Raven Press, New York, N.Y., 1992)). However, its activity appears to be excessive in some disease states and inflammatory reactions such as rheumatoid arthritis, cachexia, and septic shock (Pujol-Borrell et al., Nature 1987 326, 304–306; Oliff, Cell 1988 54, 141–142; Tracey et al., Nature 1987, 330, 662–664). The excess TNFα results in an exaggerated immune response exemplified by overstimulation of interleukin-6 and granulocyte/macrophage-colony stimulating factor (GM-CSF) secretion, enhanced cytotoxicity of polymorphonuclear neutrophils, and prolonged expression of cellular adhesion molecules, all of which can have detrimental effects. The benefits of inhibiting TNFα activity during inflammatory reactions in animal models have been demonstrated using neutralizing monoclonal antibodies to TNFα (Tracey et al., Nature 1987, 330, 662–664; Silva et al., J. Infect. Sis. 1990, 162, 421–427; and Williams et al., Proc. Natl. Acad. Sci. 1992, 89, 9784–9788).

The mechanism of action of TNFα is derived from accumulating evidence which indicates that TNFα is a regulatory cytokine with pleiotropic biological activities. These activities include: inhibition of lipoprotein lipass synthesis ("cachectin"), activation of polymorphonuclear leukocytes, inhibition of cell growth or stimulation of cell growth, cytotoxic action on certain transformed cell types, antiviral activity, stimulation of bone resorption, stimulation of collagenase and prostaglandin E2 production, and immunoregulatory actions, including activation of T cells, B cells, monocytes, thymocytes, and stimulation of the cell-surface expression of major histocompatibility complex class I and class II molecules.

TNFα is noted for its pro-inflammatory actions which result in tissue injury, such as induction of procoagulant activity on vascular endothelial cells (Pober, J. S. et al., J. Immunol. 1986, 336, 1680), increased adherence of neutrophils and lymphocytes (Pober, J. S. et al., J. Immunol. 1987, 138, 3319), and stimulation of the release of platelet activating factor from macrophages, neutrophils and vascular endothelial cells (Camussi, G. et al., J. Exp. Med. 1987, 166, 1390).

Recent evidence implicates TNFα in the pathogenesis of many infections (Cerami, A. et al., Immunol. Today 1988, 9, 28), immune disorders, neoplastic pathology, e.g., in cachexia accompanying some malignancies (Oliff, A. et al., Cell 1987, 50, 555), and in autoimmune pathologies and graft-versus host pathology (Piguet, P.-F. et al., J. Exp. Med. 1987, 166, 1280). The association of TNFα with cancer and infectious pathologies is often related to the host's catabolic state. A major problem in cancer patients is weight loss, usually associated with anorexia. The extensive wasting which results is known as "cachexia" (Kern, K. A. al., J. Parent. Enter. Nutr. 1988, 12, 286–298). Cachexia includes progressive weight loss, anorexia, and persistent erosion of body mass in response to a malignant growth. The fundamental physiological derangement may be related to a decline in food intake relative to energy expenditure. The cachectic state is thus associated with significant morbidity and is responsible for the majority of cancer mortality. A number of studies have suggested that TNFα is an important mediator of the cachexia in cancer, infectious pathology, and in other catabolic states.

TNFα is thought to play a central role in the pathophysiological consequences of Gram-negative sepsis and endotoxic shock (Michie, H. R. et al., Br. J. Surg. 1989, 76, 670–671; Debets, J. M. H. et al., Second Vienna Shock Forum, 1989, p. 463–466; Simpson, S. Q. et al., Crit. Care Clin. 1989, 5, 27–47), including fever, malaise, anorexia, and cachexia. Endotoxin is a potent monocyte/macrophage activator which stimulates production and secretion of TNFα (Kornbluth, S. K. et al., J. Immunol. 1986, 137, 2585–2591) and other cytokines. Because TNFα could mimic many biological effects of endotoxin, it was concluded to be a central mediator responsible for the clinical manifestations of endotoxin-related illness. TNFα and other monocyte-derived cytokines mediate the metabolic and neurohormonal responses to endotoxin (Michie, H. R. et al., N. Eng. J. Med. 1988, 318, 1481–1486). Endotoxin administration to human volunteers produces acute illness with flu-like symptoms including fever, tachycardia, increased metabolic rate and stress hormone release (Revhaug, A. et al., Arch. Surg. 1988, 123, 162–170). Elevated levels of circulating TNFα have also been found in patients suffering from Gram-negative sepsis (Waage, A. et al., Lancet 1987, 1, 355–357). Treatment of cancer patients with TNFα (because of its tumoricidal action) revealed that doses greater than 545 μg/m²/24 hours caused alterations similar to those induced by injection of endotoxin (4 ng/kg) into healthy humans (Michie, H. R. et al., Surgery 1988, 104, 280–286), supporting TNFα's role as the principal host mediator of septic and endotoxemic responses. Chronic intravenous TNFα infusion into humans or rats was associated with anorexia, fluid retention, acute phase responses, and negative nitrogen balance (i.e., classic catabolic effects), leading to the conclusion that TNFα may be responsible for many of the changes noted during critical illness (Michie, H. R. et al., Ann. Surg. 1989, 209, 19–24).

The numerous biological effects of TNFα and the closely related cytokine, TNFβ (lymphotoxin), are mediated by two transmembrane receptors, both of which have been cloned. The p55 receptor (also termed TNF-R55, TNF-RI, or TNFRβ) is a 55 kd glycoprotein shown to transduce signals resulting in cytotoxic, anti-viral, and proliferative activities of TNFα.

The p75 receptor (also termed TNF-R75, TNF-RII, or TNFRα) is a 75 kd glycoprotein that has also been shown to transduce cytotoxic and proliferative signals as well as signals resulting in the secretion of GM-CSF. The extracellular domains of the two receptors are 28% identical in primary structure and have in common a set of four subdomains defined by numerous conserved cysteine residues. The p75 receptor differs, however, by having a region adjacent to the transmembrane domain that is rich in proline residues and contains sites for 0-linked glycosylation. Interestingly, the cytoplasmic domains of the two receptors share no apparent homology which is consistent with observations that they can transduce different signals to the interior of the cell.

TNFα inhibitors have been detected in normal human urine and in serum of patients with cancer or endotoxemia. These have since been shown to be the receptor extracellular domains derived by proteolytic cleavage of the transmembrane forms. Many of the same stimuli that result in TNFα release also result in the release of the soluble receptors, suggesting that these soluble TNFα inhibitors may serve as part of a negative feedback mechanism to control TNFα activity (Porteu, F. and C. Nathan (1990) *J. Exp. Med.* 172: 599–607; and, Adreke, D. et al., (1992) *J. Exp. Med.* 175: 323–329).

There is a need for compounds which effectively inhibit TNFα activity. There is a need to provide compounds that bind to TNFα with high affinity and can prevent TNFα from binding to its receptors. There is a need for compounds which can neutralize TNFα activity in vivo.

SUMMARY OF THE INVENTION

The present invention relates to peptides which comprise an amino acid sequence consisting of 4 to 25 amino acids and which inhibit TNFα activity. The peptides of the invention comprises at least a four amino acid residue fragment of one of SEQ ID NO:1, SEQ ID NO:2, SEQ ID NO:17, SEQ ID NO:20, SEQ ID NO:21 or SEQ ID NO:22.

The present invention relates to a method of inhibiting tumor necrosis factor-alpha activity comprising the step of contacting tumor necrosis factor-alpha with a peptide that comprises an amino acid sequence which consists of 4 to 25 amino acids and which inhibits TNFα activity. The peptide used in the method of inhibiting tumor necrosis factor-alpha activity comprises at least a four amino acid residue fragment of one of SEQ ID NO:1, SEQ ID NO:2, SEQ ID NO:17, SEQ ID NO:20, SEQ ID NO:21 or SEQ ID NO: 22.

The present invention relates to a method of treating an animal suspected of suffering from a disease or disorder mediated by tumor necrosis factor-alpha activity comprising the step of administering to said individual a therapeutically effective amount of a peptide that inhibits tumor necrosis factor-alpha. The peptide comprises an amino acid sequence which consists of 4 to 25 amino acids and comprises at least a four amino acid residue fragment of one of SEQ ID NO:1, SEQ ID NO:2, SEQ ID NO:17, SEQ ID NO:20, SEQ ID NO:21 or SEQ ID NO:22.

DETAILED DESCRIPTION OF THE INVENTION

According to the present invention, compounds are provided which bind to the TNFα and thereby prevent it from binding to p55 and p75 receptors. By inhibiting such TNFα/TNF receptor binding, the compounds of the invention inhibit the biological activity of TNFα. By blocking TNFα from binding to its receptors, the compounds of the invention prevent TNFα from producing the biological effect associated with the TNFα-TNF receptor binding.

Compounds according to some aspects of the invention are peptides consisting of 4 to 25 amino acids. In some embodiments, the peptides consist of 20 amino acids or less. In some embodiments, the peptides consist of at least 8 amino acids. In some embodiments, the peptides consist of 8–20 amino acids. In some embodiments, the peptides consist of 10–15 amino acids.

Compounds according to some aspects of the invention are peptides consisting of 4 to 25 amino acids. In some embodiments, the peptides consist of 20 amino acids or less. In some embodiments, the peptides consist of at least 8 amino acids. In some embodiments, the peptides consist of 8, 9, 10, 11, 12, 13, 14, 15, 16, 17, 18, 19 or 20 amino acids.

In some embodiments, the peptides are conformationally restricted such as those which are cyclicized, circularized or otherwise restricted by peptide and/or non-peptide bonds to limit conformational variation and/or to increase stability and/or half-life of the peptides. In some embodiments, peptides are provided as linear peptides.

In some embodiments, peptides of the present invention comprise one or more D amino acids. As used herein, the term "D amino acid peptides" is meant to refer to peptides according to the present invention which comprise at least one and preferably a plurality of D amino acids. D amino acid peptides consist of 4–25 amino acids. D amino acid peptides retain the biological activity of the peptides of the invention that consist of L amino acids, i.e. D amino acid peptides inhibit TNFα. In some embodiments, the use of D amino acid peptides is desirable as they are less vulnerable to degradation and therefore have a longer half life.

As used herein, the term "derivatives" refers to peptides of the invention which have the amino terminal and/or the carboxy terminal blocked, particularly those in which the amino group of the N terminal residue is acetylated and/or the carboxy group of the C terminal residue is amidated.

Contemplated equivalents include conservative analogs and mimetics. As used herein, the term "conservative analog" is also meant to refer to a peptide consisting of 4–25 amino acids which inhibits TNFα and which comprises an amino acid sequence that includes at least a four amino acid sequence that is substantially identical to at least a four amino acid fragment of SEQ ID NO:1, SEQ ID NO:2, SEQ ID NO:17, SEQ ID NO:20, SEQ ID NO:21 or SEQ ID NO:22. As used herein, the term "substantially identical" refers to an amino acid sequence that is the same as the amino acid sequence of at least a four amino acid fragment of SEQ ID NO:1, SEQ ID NO:2, SEQ ID NO:17, SEQ ID NO:20, SEQ ID NO:21 or SEQ ID NO:22, except some of the residues are substituted with conservative amino acids. Conservative substitutions of amino acids are determined, for example, following what are referred to as Dayhof's rules for amino acid substitution (Dayhof, M. D. (1978) *Nat. Biomed. Res. Found.*, Washington, D.C. Vol. 5, supp. 3). Equivalent residues are listed and amino acid residues in a peptide sequence may be substituted with comparable amino acid residues. Such substitutions are well known and are based the upon charge and structural characteristics of each amino acid. Those having ordinary skill in the art can readily design and produce conservative analogs. In addition, the term "conservative analogs" is meant to encompass peptides which have amino acid that comprise at least a four amino acid fragment of SEQ ID NO:1, SEQ ID NO:2, SEQ ID NO:17, SEQ ID NO:20, SEQ ID NO:21 or SEQ ID NO:22, in which an amino acid residue from the fragment is deleted and/or an amino acid is inserted within the fragment sequence. Conservative analogs inhibit TNFα in the same manner as the peptides of the invention. By interacting with TNFα in such a way and thereby inhibiting TNFα activity, conservative analogs perform essentially the same function by essentially the same means to achieve essentially the same result as the peptides of the invention.

In addition, conservative analogs are meant to include peptides of the invention which contain one or more substitutions including substitutions which are not conservative but in which the peptide nonetheless inhibits TNFα in the same manner as the peptides of the invention. By interacting with TNFα in such a way and thereby inhibiting TNFα activity, conservative analogs perform essentially the same function by essentially the same means to achieve essentially the same result as the peptides of the invention.

In addition to conservative analogs, the present invention contemplates compounds which display substantially the same surface as the peptides of the invention. As used herein, the term "mimetics" is meant to refer to compounds that are not peptides but that comprise a similar surface as the peptides of the invention and can thus interact with the TNF receptor in a similar fashion as the peptides of the invention. Mimetics inhibit TNFα by interacting with TNFα in the same manner as the peptides of the invention. Mimetics have a molecular surface similar to one of a peptide comprising at least a four amino acid fragment of SEQ ID NO:1, SEQ ID NO:2, SEQ ID NO:17, SEQ ID NO:20, SEQ ID NO:21 or SEQ ID NO:22 and that molecular surface interacts with TNFα. By providing a similar surface involved in intermolecular interactions, mimetics perform essentially the same function by essentially the same means to achieve essentially the same result as the peptides of the invention.

According to some embodiments of the invention, peptides comprise SEQ ID NO:1. According to some embodiments of the invention, peptides consist of SEQ ID NO:1.

According to some embodiments of the present invention, peptides comprise fragments of SEQ ID NO:1 that have at least four amino acid residues. Peptides that comprise fragments of SEQ ID NO:1 may have 8, 9, 10, 11, 12, 13, 14, 15, 16, 17 or 18 amino acid residues. According to some embodiments of the present invention, peptides consist of fragments of SEQ ID NO:1 that have at least four amino acid residues. Peptides that consist of fragments of SEQ ID NO:1 may have 8, 9, 10, 11, 12, 13, 14, 15, 16, 17 or 18 amino acid residues. According to some embodiments of the present invention, peptides comprise fragments of SEQ ID NO:1. Some embodiments of the invention are conformationally restricted peptides that comprise SEQ ID NO:1 or fragments thereof. The peptides may be cyclicized to facilitate restricted conformations. In some embodiments, cysteine residues are provided to form disulfide bonds to achieve cyclization. Some embodiments of the invention provide derivatized peptides which comprise or consist of SEQ ID NO:1 or fragments of SEQ ID NO:1 that have at least four amino acids.

According to some embodiments of the invention, peptides comprise SEQ ID NO:2. According to some embodiments of the invention, peptides consist of SEQ ID NO:2. According to some embodiments of the present invention, peptides comprise fragments of SEQ ID NO:2 that have at least four amino acid residues. Peptides that comprise fragments of SEQ ID NO:2 may have 8, 9, 10, 11, 12, 13, 14, 15, 16, 17 or 18 amino acid residues. According to some embodiments of the present invention, peptides consist of fragments of SEQ ID NO:2 that have at least four amino acid residues. Peptides that consist of fragments of SEQ ID NO:2 may have 8, 9, 10, 11, 12, 13, 14, 15, 16, 17 or 18 amino acid residues. An examples of peptides which consists of fragment of SEQ ID NO:2 include SEQ ID NO:7. According to some embodiments of the present invention, peptides comprise fragments of SEQ ID NO:2. Examples of peptides that comprise a fragment of SEQ ID NO:2 include SEQ ID NO:3, SEQ ID NO:4, SEQ ID NO:5, SEQ ID NO:6, SEQ ID NO:8, SEQ ID NO:9, SEQ ID NO:10, SEQ ID NO:11, SEQ ID NO:12, SEQ ID NO:13, SEQ ID NO:14, SEQ ID NO:15 and SEQ ID NO:16.

Some embodiments of the invention are conformationally restricted peptides that comprise SEQ ID NO:2 of fragments thereof. The peptides may be cyclicized to facilitate restricted conformations. In some embodiments, cysteine residues are provided to form disulfide bonds to achieve cyclization.

Some embodiments of the invention provide derivatized peptides which comprise or consist of SEQ ID NO:2 or fragments of SEQ ID NO:13 that have at least four amino acids. Example of a derivatized peptide are N-terminal acetylated SEQ ID NO:2 and N-terminal acetylated SEQ ID NO:5.

According to some embodiments of the invention, peptides consist of SEQ ID NO:17. According to some embodiments of the invention, peptides comprise SEQ ID NO:17. An examples of a peptide that comprise SEQ ID NO:17 is SEQ ID NO:18.

According to some embodiments of the present invention, peptides comprise fragments of SEQ ID NO:17 that have at least four amino acid residues. Peptides that comprise fragments of SEQ ID NO:17 may have 8, 9, 10, 11, 12, 13, 14, 15, 16, 17 or 18 amino acid residues. According to some embodiments of the present invention, peptides consist of fragments of SEQ ID NO:17 that have at least four amino acid residues. Peptides that consist of fragments of SEQ ID NO:17 may have 8, 9, 10, 11, 12, 13, 14, 15, 16, 17 or 18 amino acid residues. According to some embodiments of the present invention, peptides comprise fragments of SEQ ID NO:17. An example of a peptide that comprises a fragment of SEQ ID NO:17 is SEQ ID NO:19.

Some embodiments of the invention are conformationally restricted peptides that comprise SEQ ID NO:17 or fragments thereof. The peptides may be cyclicized to facilitate restricted conformations. In some embodiments, cysteine residues are provided to form disulfide bonds to achieve cyclization.

Some embodiments of the invention provide derivatized peptides which comprise or consist of SEQ ID NO:17 or fragments of SEQ ID NO:17 that have at least four amino acids. Examples of a derivatized peptides are N-terminal acetylated SEQ ID NO:17, N-terminal acetylated SEQ ID NO:17, N-terminal acetylated SEQ ID NO:18 and N-terminal acetylated SEQ ID NO:19.

According to some embodiments of the invention, peptides consist of SEQ ID NO:20. According to some embodiments of the invention, peptides comprise SEQ ID NO:20. According to some embodiments of the present invention, peptides comprise fragments of SEQ ID NO:20 that have at least four amino acid residues. Peptides that comprise fragments of SEQ ID NO:27 may have 8, 9, 10, 11, 12, 13, 14, 15, 16, 17 or 18 amino acid residues. According to some embodiments of the present invention, peptides consist of fragments of SEQ ID NO:20 that have at least four amino acid residues. Peptides that consist of fragments of SEQ ID NO:27 may have 8, 9, 10, 11, 12, 13, 14, 15, 16, 17 or 18 amino acid residues. According to some embodiments of the present invention, peptides comprise fragments of SEQ ID NO:20. Some embodiments of the invention are conformationally restricted peptides that comprise SEQ ID NO:20 or fragments thereof. The peptides may be cyclicized to facilitate restricted conformations. In some embodiments, cysteine residues are provided to form disulfide bonds to achieve cyclization. Some embodiments of the invention provide derivatized peptides which comprise or consist of SEQ ID NO:20 or fragments of SEQ ID NO:20 that have at least four amino acids. An example of a derivatized peptide is N-terminal acetylated SEQ ID N0:20.

According to some embodiments of the invention, peptides consist of SEQ ID NO:21. According to some embodiments of the invention, peptides comprise SEQ ID NO:21. According to some embodiments of the present invention, peptides comprise fragments of SEQ ID NO:21 that have at least four amino acid residues. Peptides that comprise fragments of SEQ ID NO:21 may have 8, 9, 10, 11, 12, 13, 14, 15, 16, 17 or 18 amino acid residues. According to some embodiments of the present invention, peptides consist of fragments of SEQ ID NO:21 that have at least four amino acid residues. Peptides that consist of fragments of SEQ ID NO:21 may have 8, 9, 10, 11, 12, 13, 14, 15, 16, 17 or 18 amino acid residues. According to some embodiments of the present invention, peptides comprise fragments of SEQ ID NO:21. Some embodiments of the invention are conformationally restricted peptides that comprise SEQ ID NO:21 or fragments thereof. The peptides may be cyclicized to facilitate restricted conformations. In some embodiments, cysteine residues are provided to form disulfide bonds to achieve cyclization. Some embodiments of the invention provide derivatized peptides which comprise or consist of SEQ ID NO:21 or fragments of SEQ ID NO:21 that have at least four amino acids.

According to some embodiments of the invention, peptides consist of SEQ ID NO:22. According to some embodiments of the invention, peptides comprise SEQ ID NO:22. According to some embodiments of the present invention, peptides comprise fragments of SEQ ID NO:22 that have at least four amino acid residues. Peptides that comprise fragments of SEQ ID NO:22 may have 8, 9, 10, 11, 12, 13, 14, 15, 16, 17 or 18 amino acid residues. According to some embodiments of the present invention, peptides consist of fragments of SEQ ID NO:22 that have at least four amino acid residues. Peptides that consist of fragments of SEQ ID NO:22 may have 8, 9, 10, 11, 12, 13, 14, 15, 16, 17 or 18 amino acid residues. According to some embodiments of the present invention, peptides comprise fragments of SEQ ID NO:22. Some embodiments of the invention are conformationally restricted peptides that comprise SEQ ID NO:22 or fragments thereof. The peptides may be cyclicized to facilitate restricted conformations. In some embodiments, cysteine residues are provided to form disulfide bonds to achieve cyclization. Some embodiments of the invention provide derivatized peptides which comprise or consist of SEQ ID NO:22 or fragments of SEQ ID NO:22 that have at least four amino acids.

Peptides of the invention, including D amino acid peptides, may be prepared using the solid-phase synthetic technique initially described by Merrifield, in *J. Am. Chem. Soc.*, 15: 2149–2154 (1963). Other peptide synthesis techniques may be found, for example, in M. Bodanszky et al., (1976) *Peptide Synthesis*, John Wiley & Sons, 2d Ed.; Kent and Clark-Lewis in Synthetic Peptides in Biology and Medicine, p. 295–358, eds. Alitalo, K., et al. *Science Publishers*, (Amsterdam, 1985); as well as other reference works known to those skilled in the art. A summary of peptide synthesis techniques may be found in J. Stuart and J. D. Young, *Solid Phase Peptide Synthelia*, Pierce Chemical Company, Rockford, Ill. (1984), which is incorporated herein by reference. The synthesis of peptides by solution methods may also be used, as described in *The Proteins*, Vol. II, 3d Ed., p. 105–237, Neurath, H. et al., Eds., Academic Press, New York, N.Y. (1976). Appropriate protective groups for use in such syntheses will be found in the above texts, as well as in J. F. W. McOmie, *Protective Groups in Organic Chemistry*, Plenum Press, New York, N.Y. (1973), which is incorporated herein by reference. In general, these synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Block synthesis techniques may also be applied to both the solid phase and solution methods of peptide synthesis. Rather than sequential addition of single amino acid residues, preformed blocks comprising two or more amino acid residues in sequence are used as either starting subunits or subsequently added units rather than single amino acid residues.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

In order to determine whether a peptide inhibits TNFα, one or more of several assays may be performed. Included among these are assays which measure the ability a TNFα inhibitor candidate, i.e. a test compound, to inhibit TNFα from binding to a fusion protein that is composed of a TNF receptor or a TNFα-binding portion thereof, fused to an immunoglobulin molecule or a portion thereof. In other assays, the ability a test compound to inhibit TNFα from binding to an isolated TNF receptor is measured. Other assays include those which the ability of a TNFα inhibitor candidate, i.e. a test compound, to inhibit TNFα activity when TNFα is contacted with cells that react to the presence of TNFα. For example, TNFα is cytotoxic to some cells, such as WEHI cells, and assays can be used to measure the ability a test compound, to inhibit TNFα cytotoxicity.

There are numerous other assays which can be used to determine a test compound's ability to inhibit TNFα. In some assays, specific non-lethal effects of TNFα on some cells is used as an end point to evaluate the TNFα inhibitory activity of a test compound. Known effects of TNFα on fibroblast cells include effects on mitogenesis, IL-6 secretion and HLA class II antigen induction. Comparisons can be made between TNFα's effect on fibroblasts in the presence or absence of a test compound using these detectable phenotypic changes as endpoints. Similarly, known effects of TNFα on monocyte cells include effects on secretion of cytokines such as GMCSF, IL-6 and IL-8. Comparisons can be made between TNFα's effect on cytokine secretion by monocytes in the presence or absence of a test compound. Additionally, TNFα is known to have effects on secretion of cytokine by endothelial cells and similar assays may be designed and performed. Further, TNFα is also known to effect adhesion molecule induction, ICAM-1, E-selectin, VCAM and tissue factor production in endothelial cells. Comparisons can be made between TNFα's effect on endothelial cells in the presence or absence of a test compound using these detectable phenotypic changes as endpoints as well. Likewise, TNFα is known to effect neutrophils in specific ways. Comparisons can be made between TNFα's effect on neutrophils in the presence or absence of a test compound using activation, priming, degranulation and superoxide production as detectable endpoints for evaluation of TNFα inhibitory activity. These and other assays are well known to those having ordinary skill in the art. Such assays may be designed and performed routinely form readily available starting materials.

The TNFα inhibitors according to the invention are useful for treating a vertebrate having a pathology or condition associated with levels of a substance reactive with a TNF receptor, in particular TNFα, in excess of the levels present in a normal healthy subject. Such pathologies include, but are not limited to: sepsis syndrome, including cachexia; circulatory collapse and shock resulting from acute or chronic bacterial infection; acute and chronic parasitic or infectious processes, including bacterial, vital and fungal infections; acute and chronic immune and autoimmune pathologies, such as systemic lupus erythematosus and rheumatoid arthritis; alcohol-induced hepatitis; chronic inflammatory pathologies such as sarcoidosis and Crohn's pathology; vascular inflammatory pathologies such as disseminated intravascular coagulation; graft-versus-host pathology; Rawasaki's pathology; and malignant pathologies involving TNFα-secreting tumors.

Such treatment comprises administering a single or multiple doses of the compounds of the invention. Preferred for human pharmaceutical use are pharmaceutical compositions that comprise the compounds of the present invention in combination with a pharmaceutically acceptable carrier or diluent.

The pharmaceutical compositions of the present invention may be administered by any means that enables the active agent to reach the agent's site of action in the body of a mammal. In the case of the peptides of the invention, the primary focus is the ability to reach and bind with TNFα. Because proteins are subject to being digested when administered orally, parenteral administration, i.e., intravenous, subcutaneous, intramuscular, would ordinarily be used to optimize absorption. In some preferred embodiments, pharmaceutical compositions which comprise the compounds of the present invention are administered intravenously or subcutaneously.

Pharmaceutical compositions of the present invention may be administered either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.001 to 1 grams per kilogram of body weight, in some embodiments about 0.1 to 100 milligrams per kilogram of body weight. Ordinarily dosages are in the range of 0.5 to 50 milligrams per kilogram of body weight, and preferably 1 to 10 milligrams per kilogram per day. In some embodiments, the pharmaceutical compositions are given in divided doses 1 to 6 times a day or in sustained release form is effective to obtain desired results.

Dosage forms (composition) suitable for internal administration generally contain from about 1 milligram to about 500 milligrams of active ingredient per unit. In these pharmaceutical compositions the active ingredient will ordinarily be present in an amount of about 0.5–95 by weight based on the total weight of the composition.

For parenteral administration, the TNFα inhibitor can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

Suitable pharmaceutical carriers are described in the most recent edition of *Remington's Pharmaceutical Sciences*, A. Osol, a standard reference text in this field.

For example, a parenteral composition suitable for administration by injection is prepared by dissolving 1.5% by weight of active ingredient in 0.9% sodium chloride solution.

EXAMPLES

Example 1 p55 Receptor/IgG Fusion Protein Binding Assay

In order to screen compounds for their ability to block TNFα binding to the TNF p55 receptor, an assay has been designed using TNFα and a p55/IgG fusion protein in place of monovalent, non-fusion p55 TNF receptor protein. This assay was designed to identify peptides which bind to human TNFα and thereby prevent the capture of the TNFα by a microtiter plate coated with p55-Ig fusion protein. A constant concentration of human TNFα is preincubated with the test peptide and then incubated on the p55-Ig coated microtiter wells. Bound TNFα is detected using a specific antisera and an alkaline phosphatase-conjugated probe. An active peptide will reduce the amount of human TNFα bound to the well relative to control wells in which TNFα but no peptide was added.

A 96-well, U-bottom polyvinylchloride microtiter plate was coated with 50 µl/well of p55-Ig fusion protein at 5 µg/ml in 0.01M sodium phosphate, 0.15M sodium chloride (PBS) by incubation overnight at 4° C. or 2 hours at 37° C. The fusion protein, which consists of a p55 TNF receptor protein portion and an IgG portion, can be produced as disclosed in U.S. application Ser. No. 08/010,406 filed Jan. 29, 1993 which is incorporated herein by reference. The plate was washed three times with 0.05% Tween-20 in PBS, then blocked, by adding 150 µl/well of assay buffer (10 mM N-2-hydroxyethylpiperazine-N'-3-propanesulfonic acid (HEPES) pH 7.2, containing 0.1% porcine gelatin, 0.1% Tween-80, and 0.01% sodium azide) and continuing incubation for 1 hour at 37° C. or at 4° C. for 1–7 days.

Lyophilized peptides to be tested were weighed in tared 12×75 mm polystyrene tubes and reconstituted to a concentration of 1.2 mM with assay buffer. Each suspension was sonicated in a water bath for 1–5 minutes and vortexed 15–30 seconds to disperse large particles. Serial dilutions of each peptide suspension were prepared using assay buffer in a 96-well polystyrene microtiter plate. Additional wells received Fab fragment of the mouse/human monoclonal anti-human TNFα antibody cA2 (positive control) or assay buffer (negative control). Human recombinant TNFα (Biosource, Camarillo, Calif.) was added to all wells to give a final TNFα concentration of 25 ng/ml, final peptide concentrations of 1.0, 0.33 and 0.11 mM and a final cA2 Fab concentration of 500 ng/ml. The polystyrene dilution plate was then sealed and incubated 1 hour at room temperature on an orbital mixer set at moderate speed.

Following the sample preincubation, blocker was discarded from the p55-Ig coated plate and blotted dry. Aliquots (50 µl) of each peptide or control were transferred into duplicate wells on the p55-Ig coated plate which was then sealed and incubated 1 hour at 37° C. Duplicate wells containing only assay buffer were included as a plate blank. After incubation the p55-Ig plate was washed three times with 0.05% Tween-20 in PBS.

To detect TNFα captured by the p55-Ig plate, all wells were incubated in succession with polyclonal rabbit anti-human TNFα (Genzyme, Boston, Mass.; 1:500 in assay buffer, 50 µl/well), biotinylated goat anti-rabbit Ig (H&L) (Vector Laboratories, Burlingame, Calif.; 1 µg/ml in assay buffer, 50 µl/well) and streptavidin-alkaline phosphatase conjugate (Pierce, Rockford, Ill.; 1 µg/ml in assay buffer, 50 µl/well). All incubations were for 1 hour at 37° C. and after each incubation the plate was washed three times with 0.05% Tween-20 in PBS. Fifty microliters of alkaline phosphatase substrate solution (alkaline buffer (Sigma, St. Louis, Mo.) diluted 1:500 in deionized water plus one 5 mg tablet of p-nitrophenyl phosphate (Sigma, St. Louis, Mo.) per 5 ml of diluted buffer) was added to all wells and incubation continued for 20 minutes at room temperature. Color development was stopped by adding to all wells 50 µl of 3N sodium hydroxide. The optical density (OD) at 405 nm was measured on a microtiter plate reader (Molecular Devices Vmax plate reader), with the plate blank wells subtracted as background. The activity of each peptide was then expressed as the percent inhibition of TNFα capture by the p55-Ig plate, relative to the amount of TNFα captured in wells containing only assay buffer (negative control), as follows:

% inhibition=100−((mean OD peptide/mean OD negative control)×100).

The validity of each assay was confirmed by the cA2 Fab positive control which typically inhibited TNFα capture by more than ≧75%.

Example 2

The inhibition of binding of TNFα to p55TNFr-IgG chimeric construct was performed as described above using several embodiments of the invention. The peptides were tested to determine the concentration necessary to inhibit TNFα by 50% ($IC_{50}$) relative to TNFα activity in the absence of the peptide. The following data were generated.

The $IC_{50}$ of SEQ ID NO:1 in which the amino terminal asparagine is acetyl asparagine and the carboxy terminal glycine is glycine amide was 20 µM. The minimum $IC_{50}$ observed for SEQ ID NO:1 in which the amino terminal asparagine is acetyl asparagine and the carboxy terminal glycine is glycine amide was 8 µM and the maximum $IC_{50}$ observed for SEQ ID NO:1 in which the amino terminal asparagine is acetyl asparagine and the carboxy terminal glycine is glycine amide was 91 µM.

The $IC_{50}$ of SEQ ID NO:2 in which the amino terminal serine is acetyl serine and the carboxy terminal tryptophan is tryptophan amide was 29 µM. The minimum $IC_{50}$ observed for SEQ ID NO:2 in which the amino terminal serine is acetyl serine and the carboxy terminal tryptophan is tryptophan amide was 9 µM and the maximum $IC_{50}$ observed for SEQ ID NO:2 in which the amino terminal serine is acetyl serine and the carboxy terminal tryptophan is tryptophan amide was 60 µM.

The $IC_{50}$ of SEQ ID NO:3 in which the carboxy terminal tryptophan is tryptophan amide was 23 µM. The minimum $IC_{50}$ observed for SEQ ID NO:3 in which the carboxy terminal tryptophan is tryptophan amide was 10 µM and the maximum $IC_{50}$ observed for SEQ ID NO:3 in which the amino terminal serine is acetyl serine and the carboxy terminal tryptophan is tryptophan amide was 33 µM.

The $IC_{50}$ of SEQ ID NO:4 in which the carboxy terminal alanine is alanine amide was 80 µM. The minimum $IC_{50}$ observed for SEQ ID NO:4 in which the carboxy terminal alanine is alanine amide was 74 µM and the maximum $IC_{50}$ observed for SEQ ID NO:4 in which the carboxy terminal alanine is alanine amide was 87 µM.

The $IC_{50}$ of SEQ ID NO:17 in which the amino terminal leucine is acetyl leucine and the carboxy terminal glycine is glycine amide was 155 µM. The minimum $IC_{50}$ observed for SEQ ID NO:17 in which the amino terminal leucine is acetyl leucine and the carboxy terminal glycine is glycine amide was 51 µM and the maximum $IC_{50}$ observed for SEQ ID NO:17 in which the amino terminal leucine is acetyl leucine and the carboxy terminal glycine is glycine amide was 210 µM.

The $IC_{50}$ of SEQ ID NO:18 in which the amino terminal leucine is acetyl leucine and the carboxy terminal valine is valine amide was 307 µM. The minimum $IC_{50}$ observed for SEQ ID NO:18 in which the amino terminal leucine is acetyl leucine and the carboxy terminal valine is valine amide was 29 µM and the maximum $IC_{50}$ observed for SEQ ID NO:18 in which the amino terminal leucine is acetyl leucine and the carboxy terminal valine is valine amide was 829 µM.

The $IC_{50}$ of SEQ ID NO:20 in which the amino terminal valine is acetyl valine and the carboxy terminal serine is serine amide was 86 µM. The minimum $IC_{50}$ observed for SEQ ID NO:20 in which the amino terminal valine is acetyl valine and the carboxy terminal serine is serine amide was 37 µM and the maximum $IC_{50}$ observed for SEQ ID NO:20 in which the amino terminal valine is acetyl valine and the carboxy terminal serine is serine amide was 150 µM.

Example 3 Treatment of Arthritis, Sepsis, Allograft Rejection and Graft Versus Host Disease In rheumatoid arthritis, the main presenting symptoms are pain, stiffness, swelling, and loss of function (Bennett J C. The etiology of rheumatoid arthritis, in *Textbook of*

Rheumatology, Kelley W N, Harris E D, Ruddy S, Sledge C B, Eds., W B Saunders, Philadelphia, 1985, pp 879–886). The multitude of drugs used in controlling such symptoms seems largely to reflect the fact that none is ideal. Although there have been many years of intense research into the biochemical, genetic, microbiological, and immunological aspects of rheumatoid arthritis, its pathogenesis is not completely understood, and none of the treatments clearly stop progression of joint destruction (Harris ED, Rheumatoid Arthritis: The clinical spectrum, in *Textbook of Rheumatology*, Kelley W N, Harris E D, Ruddy S, Sledge C B, Eds., W B Saunders, Philadelphia, 1985, pp 915–990).

TNFα is of major importance in the pathogenesis of rheumatoid arthritis. TNFα is present in rheumatoid arthritis joint tissues and synovial fluid at the protein and mRNA level (Buchan G, Barrett K, Turner M, Chantry D, Naini R N, and Feldmann N., Interleukin-1 and tumor necrosis factor mRNA expression in rheumatoid arthritis: prolonged production of IL-1α, *Clin. Exp. Immunol.* 1988, 73, 449–455), indicating local synthesis. However, detecting TNFα in rheumatoid arthritis joints even in quantities sufficient for bioactivation does not necessarily indicate that it is important in the pathogenesis of rheumatoid arthritis, nor that it is a good candidate therapeutic target. In order to address these questions, the effects of anti-TNFα antibody (rabbit or monoclonal) on rheumatoid joint cell cultures, and for comparison, osteoarthritic cell cultures, have been studied. The initial result, that IL-I production was abolished, suggested that TNFα was a therapeutic target for the therapy of rheumatoid arthritis, since anti-TNFα would block both TNFα and IL-I, the two cytokines known to be involved in cartilage and bone destruction (Brennan F M, Chantry D, Jackson A, Maini R N, and Feldmann M, Inhibitory effect of TNFα antibodies on synovial cell interleukin-1 production in rheumatoid arthritis, *Lancet* 1989, II, 244–247).

Subsequent studies in rheumatoid arthritis tissues have supported this hypothesis. Thus it was found that anti-TNFα abrogated the production of another proinflammatory cytokine, GM-CSF (Haworth C, Brennan F M, Chantry D, Maini R N, and Feldmann M, GM-CSF expression in rheumatoid arthritis: regulation by tumor necrosis factor alpha, *Eur. J. Immunol.* 1991, 21, 2575–2579). This observation has been independently confirmed (Alvaro-Gracia et al., Cytokines in chronic inflammatory arthritis, VI. 1991, Analysis of synovial cell involved in granulocyte-macrophage colony-stimulating factor production and gene expression in rheumatoid arthritis and its regulation by IL-I and tumor necrosis factor-s). It has also been demonstrated that anti-TNFα diminishes cell adhesion and HLA class II expression in rheumatoid arthritis joint cell cultures.

Example 4 Treatment of HIV Infection

TNFα is capable of inducing HIV expression in HIV-infected cell lines. See Poli et al., *Proc. Natl. Acad. Sci. U.S.A.* 1990 87, 782–785 and Butera et al., *J. Immunology* 1993 150, 625–634. Butera et al. demonstrated a reduction of induced TNFα production and HIV expression in an infected cell line after treatment with soluble TNF receptors. Thus, the molecules of the present invention may be used to decrease the expression of TNFα and thereby lessen the induction of HIV expression.

Example 5 Diagnostic Methods

The present invention also provides the peptide-based inhibitors of TNFα including fragments, derivatives, and mimetics thereof which are detectably labeled, as described below, for use in diagnostic methods for detecting TNFα in patients known to be or suspected of having a TNFα-mediated condition.

The detectably labelled molecules of the present invention are useful for immunoassays which detect or quantitate TNFα in a sample. An immunoassay for TNFα typically comprises incubating a biological sample in the presence of a detectably labeled high affinity molecule of the present invention capable of selectively binding to TNF, and detecting the labeled molecules which is bound in a sample. Various clinical immunoassay procedures are described in *Immunoassays for the 80's*, A. Voller et al., Eds., University Park, 1981.

Thus, in this aspect of the invention, the molecule or a biological sample may be added to nitrocellulose, or other solid support which is capable of immobilizing cells, cell particles or soluble proteins. The support may then be washed with suitable buffers followed by treatment with the detectably labeled TNFα-specific antibody. The solid phase support may then be washed with the buffer a second time to remove unbound antibody. The amount of bound label on said solid support may then be detected by conventional means.

By "solid phase support" or "carrier" is intended any support capable of binding TNFα proteins or molecules of the present invention. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to TNFα or an anti-TNFα antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding TNFα or compounds of the invention, or will be able to ascertain the same by use of routine experimentation.

The binding activity of a given lot of anti-TNFα compound may be determined according to well known methods. Those skilled in the art will be able to determine operative and optimal assay conditions for each determination by employing routine experimentation.

One of the ways in which the TNFα-specific molecule can be detectably labeled is by linking the same to an enzyme and use in an enzyme immunoassay (EIA), or enzyme-linked immunosorbent assay (ELISA). This enzyme, when subsequently exposed to its substrate, will react with the substrate generating a chemical moiety which can be detected, for example, by spectrophotometric, fluorometric or by visual means. Enzymes which can be used to detectably label the TNFα-specific molecules of the present invention include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. By radioactively labeling the TNFα-specific molecules, it is possible to detect TNFα through the use of a radioimmunoassay (RIA) (see, for example, Work, T. S., et al., *Laboratory Techniques and Biochemistry in Molecular Biology*, North Holland Publishing Company, N.Y., 1978. The radioactive isotope can be detected by such means as the use of a gamma counter or a scintillation counter or by autoradiography. Isotopes which are particularly useful for the purpose of the present invention are: $^{3}H$, $^{125}I$, $^{131}I$, $^{35}S$, $^{14}C$, and, preferably, $^{125}I$.

It is also possible to label the TNFα-specific molecules with a fluorescent compound. When the fluorescent labeled compound is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, ophthaldehyde and fluorescamine.

The TNFα-specific molecules can also be detectably labeled using fluorescence-emitting metals such as $^{152}Eu$, or others of the lanthanide series. These metals can be attached to the TNFα-specific molecule using such metal chelating groups as diethylenetriaminepentaacetic acid (DTPA) or ethylenediamine-tetraacetic acid (EDTA).

The TNFα-specific molecules also can be detectably labeled by coupling to a chemiluminescent compound. The presence of the chemiluminescently labeled compound is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the TNFα-specific molecule, fragment or derivative of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. Detection of the TNFα-specific compound, fragment or derivative may be accomplished by a scintillation counter, for example, if the detectable label is a radioactive gamma emitter, or by a fluorometer, for example, if the label is a fluorescent material. In the case of an enzyme label, the detection can be accomplished by colorometric methods which employ a substrate for the enzyme. Detection may also be accomplished by visual comparison of the extent of enzymatic reaction of a substrate in comparison with similarly prepared standards.

Another way of detectably labelling peptides is by biotinylation. The means of labelling peptides with biotin and of detecting biotinylated peptides with avidin or streptavidin conjugate are well known. Biotinylated peptides may be can be captured using streptavidin coated plates. Those having ordinary skill in the art can readily practice the present invention using biotin detection and capture means.

For the purposes of the present invention, the TNFα which is detected by the above assays may be present in a biological sample. Any sample containing TNFα can be used. Preferably, the sample is a biological fluid such as, for example, blood, serum, lymph, urine, inflammatory exudate, cerebrospinal fluid, amniotic fluid, a tissue extract or homogenate, and the like. However, the invention is not limited to assays using only these samples, it being possible for one of ordinary skill in the art to determine suitable conditions which allow the use of other samples.

In situ detection may be accomplished by removing a histological specimen from a patient, and providing the combination of labeled antibodies of the present invention to such a specimen. The peptide is preferably provided by applying or by overlaying the labeled molecule (or fragment) to a biological sample. Through the use of such a procedure, it is possible to determine not only the presence of TNFα but also the distribution of TNFα in the examined tissue. Using the present invention, those of ordinary skill will readily perceive that any of a wide variety of histological methods (such as staining procedures) can be modified in order to achieve such in situ detection. The peptide, fragment or derivative of the present invention may be adapted for utilization in an immunometric assay, also known as a "two-site" or "sandwich" assay. In a typical immunometric assay, a quantity of unlabeled peptide (or fragment of the peptide) is bound to a solid support that is insoluble in the fluid being tested and a quantity of detectably labeled soluble antibody is added to permit detection and/or quantitation of the ternary complex formed between solid-phase peptide, TNFα, and labeled anti-TNFα antibody.

Typical and preferred immunometric assays include "forward" assays in which the peptide of the invention bound to the solid phase is first contacted with the sample being tested to extract the TNFα from the sample by formation of a binary solid phase peptide-TNFα complex. After a suitable incubation period, the solid support is washed to remove the residue of the fluid sample, including unreacted TNFα, if any, and then contacted with the solution containing a known quantity of labeled peptide (which functions as a "reporter molecule"). After a second incubation period to permit the labeled peptide to complex with the TNFα bound to the solid support through the unlabeled peptide, the solid support is washed a second time to remove the unreacted labeled peptide. This type of forward sandwich assay may be a simple "yes/no" assay to determine whether TNFα is present or may be made quantitative by comparing the measure of labeled peptide with that obtained for a standard sample containing known quantities of TNFα. Such "two-site" or "sandwich" assays are described by Wide, *Radioimmune Assay Method*, Kirkham, Ed., E. & S. Livingstone, Edinburgh, 1970, pp. 199–206).

Other type of "sandwich" assays, which may also be useful with TNFα, are the so-called' "simultaneous" and "reverse" assays. A simultaneous assay involves a single incubation step wherein the peptide bound to the solid support and labeled peptide are both added to the sample being tested at the same time. After the incubation is completed, the solid support is washed to remove the residue of fluid sample and uncomplexed labeled peptide. The presence of labeled peptide associated with the solid support is then determined as it would be in a conventional "forward" sandwich assay.

In the "reverse" assay, stepwise addition first of a solution of labeled peptide to the fluid sample followed by the addition of unlabeled antibody bound to a solid support after a suitable incubation period, is utilized. After a second incubation, the solid phase is washed in conventional fashion to free it of the residue of the sample being tested and the solution of unreacted labeled peptide. The determination of labeled peptide associated with a solid support is then determined as in the "simultaneous" and "forward" assays. In one embodiment, a combination of peptide of the present invention specific for separate epitopes may be used to construct a sensitive three-site immunoradiometric assay.

I claim:

1. A peptide which inhibits tumor necrosis factor-alpha activity, wherein said peptide consist of SEQ ID NO:1.

2. The peptide of claim 1 wherein said peptide is a conformationally restricted peptide.

3. The peptide of claim 1 wherein said peptide is a derivatized peptide selected from the group consisting of: N-terminal acetylated SEQ ID NO:1.

4. A method of inhibiting tumor necrosis factor activity comprising contacting tumor necrosis factor alpha with a peptide according to claim 1.

5. The method of claim 4 wherein said peptide is a conformationally restricted peptide.

6. The method of claim 4 wherein said peptide is a derivatized peptide selected from the group consisting of: N-terminal acetylated SEQ ID NO:1.

7. A method of treating an animal suspected of suffering from a disease or disorder mediated by tumor necrosis factor-alpha activity comprising the step of administering to said individual a therapeutically effective amount of a peptide accordinq to claim 1.

8. The method of claim 7 wherein said peptide is a conformationally restricted peptide.

9. The method of claim 7 wherein said peptide is a derivatized peptide selected from the group consisting of: N-terminal acetylated SEQ ID NO:1.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
       ( A ) LENGTH: 19 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:1:

```
Asn  Ile  Asn  Pro  Asn  Asn  Gly  Gly  Thr  Ile  Tyr  Asn  Gln  Phe  Lys  Phe
 1               5                        10                          15
Gly  Lys  Gly
```

( 2 ) INFORMATION FOR SEQ ID NO:2:

( i ) SEQUENCE CHARACTERISTICS:
       ( A ) LENGTH: 11 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:2:

```
Ser  Ala  Ser  Ser  Ser  Val  Ser  Phe  Met  Tyr  Trp
 1               5                        10
```

( 2 ) INFORMATION FOR SEQ ID NO:3:

( i ) SEQUENCE CHARACTERISTICS:
       ( A ) LENGTH: 11 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:3:

```
Ser  Ala  Ala  Ser  Ser  Val  Ser  Phe  Met  Tyr  Trp
 1               5                        10
```

( 2 ) INFORMATION FOR SEQ ID NO:4:

( i ) SEQUENCE CHARACTERISTICS:
       ( A ) LENGTH: 11 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:4:

```
Ser  Ala  Ser  Ser  Ser  Val  Ser  Phe  Met  Tyr  Ala
 1               5                        10
```

( 2 ) INFORMATION FOR SEQ ID NO:5:

( i ) SEQUENCE CHARACTERISTICS:
       ( A ) LENGTH: 10 amino acids
       ( B ) TYPE: amino acid
       ( C ) STRANDEDNESS: single (D) TOPOLOGY: linear (ii) MOLECULE TYPE: peptide (xi) SEQUENCE DESCRIPTION: SEQ ID NO:5:

Ala Ala Ser Ser Val Ser Phe Met Tyr Trp
1               5                   10

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Ala Ser Ser Val Ser Phe Met Tyr Trp
1           5

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Ser Ser Val Ser Phe Met Tyr Trp
1           5

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

His Ala Ser Ser Ser Val Ser Phe Met Tyr Trp
1               5                   10

(2) INFORMATION FOR SEQ ID NO:9:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Ser His Ser Ser Ser Val Ser Phe Met Tyr Trp
1               5                   10

(2) INFORMATION FOR SEQ ID NO:10:

(i) SEQUENCE CHARACTERISTICS:
        (A) LENGTH: 11 amino acids
        (B) TYPE: amino acid
        (C) STRANDEDNESS: single ( D ) TOPOLOGY: linear ( i i ) MOLECULE TYPE: peptide ( x i ) SEQUENCE DESCRIPTION: SEQ ID NO:10:

```
Ser Ala His Ser Ser Val Ser Phe Met Tyr Trp
1               5                   10
```

( 2 ) INFORMATION FOR SEQ ID NO:11:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Ser Ala Ser His Ser Val Ser Phe Met Tyr Trp
1               5                   10
```

( 2 ) INFORMATION FOR SEQ ID NO:12:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Ser Ala Ser Ser His Val Ser Phe Met Tyr Trp
1               5                   10
```

( 2 ) INFORMATION FOR SEQ ID NO:13:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Ser Ala Ser Ser Ser His Ser Phe Met Tyr Trp
1               5                   10
```

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Ser Ala Ser Ser Ser Val Ser Phe His Tyr Trp
1               5                   10
```

( 2 ) INFORMATION FOR SEQ ID NO:15:

( i ) SEQUENCE CHARACTERISTICS:
        ( A ) LENGTH: 11 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:15:

```
Ser Lys Ser Ser Ser Val Ser Phe Met Tyr Trp
1               5                   10
```

(2) INFORMATION FOR SEQ ID NO:16:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Ser Ala Ser Lys Ser Val Ser Phe Met Tyr Trp
1               5                   10
```

(2) INFORMATION FOR SEQ ID NO:17:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Leu Leu Ile Tyr Tyr Val Ser Asn Arg Tyr Thr Gly
1               5                   10
```

(2) INFORMATION FOR SEQ ID NO:18:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Leu Leu Ile Tyr Tyr Val Ser Asn Arg Tyr Thr Gly Val
1               5                   10
```

(2) INFORMATION FOR SEQ ID NO:19:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Val Leu Ile Tyr His Val Ser Asn Arg Tyr Thr Gly
1               5                   10
```

(2) INFORMATION FOR SEQ ID NO:20:

(i) SEQUENCE CHARACTERISTICS:
        (A) LENGTH: 16 amino acids
        (B) TYPE: amino acid
        (C) STRANDEDNESS: single -continued (D) TOPOLOGY: linear (ii) MOLECULE TYPE: peptide (xi) SEQUENCE DESCRIPTION: SEQ ID NO:20:

Val Ile Trp Arg Gly Gly Ser Thr Asp Tyr Asn Ala Ala Phe Met Ser
 1               5                   10                  15

(2) INFORMATION FOR SEQ ID NO:21:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:21:

Ala Arg Ser Gly Asp Ser Leu Arg Arg Leu Val Tyr Phe Asp Tyr
 1               5                   10                  15

(2) INFORMATION FOR SEQ ID NO:22:

(i) SEQUENCE CHARACTERISTICS:
      (A) LENGTH: 11 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:22:

Ser Leu Thr Gly Tyr Gly Val His Trp Val Arg
 1               5                   10